(12) United States Patent
Björk et al.

(10) Patent No.: US 7,553,849 B2
(45) Date of Patent: Jun. 30, 2009

(54) COMPOUNDS

(75) Inventors: Anders Björk, Bjärred (SE); Karl Jansson, Dalby (SE)

(73) Assignee: Active Biotech AB, Lund (SE)

( * ) Notice: Subject to any disclaimer, the term of this patent is extended or adjusted under 35 U.S.C. 154(b) by 554 days.

(21) Appl. No.: 11/152,777

(22) Filed: Jun. 15, 2005

(65) Prior Publication Data
US 2006/0004038 A1 Jan. 5, 2006

(30) Foreign Application Priority Data
Jun. 18, 2004 (SE) .................................. 0401578

(51) Int. Cl.
*A61K 31/4365* (2006.01)
*C07D 495/06* (2006.01)
(52) U.S. Cl. ...................... 514/301; 546/114
(58) Field of Classification Search ................ 546/114; 514/301
See application file for complete search history.

(56) References Cited

U.S. PATENT DOCUMENTS 5,593,943 A 1/1997 Nuebling et al.

FOREIGN PATENT DOCUMENTS

| EP | 1419772 A1 | 5/2004 |
|---|---|---|
| WO | WO 94/29295 A1 | 12/1994 |
| WO | WO 00/53610 A2 | 9/2000 |
| WO | WO 03/059912 A1 | 7/2003 |
| WO | WO 2004/019939 A1 | 3/2004 |

OTHER PUBLICATIONS

Hans-Peter Buschstaller et al "Synthesis of Novel 2-Aminothiophene-3-carboxylates by Variations of the Gewald Reaction" Chemical Monthly, vol. 132, (2001) pp. 279-293.
R.A.W. Johnstone et al "A Rapid Method of N-Alkylation of Amines" J. Chem. Soc. (C.) (1969) pp. 2223-2224.
John W. Prineas "The neuropathology of multiple sclerosis" Handbook of Clinical Neurology vol. 3 (47) (1985) pp. 213-257.
Hsing-Jang Liu et al "An improved procedure for the preparation of 3-carbomethoxy-4-oxotetrahydrothiopyran, 2- and 4-carbomethoxy-3-oxotetrahydrothiophene" Can. J. Chem. vol. 60, (19982) pp. 437-439.

*Primary Examiner*—Patricia L Morris
(74) *Attorney, Agent, or Firm*—Browdy and Neimark, P.L.L.C.

(57) ABSTRACT

A compound of formula (I)

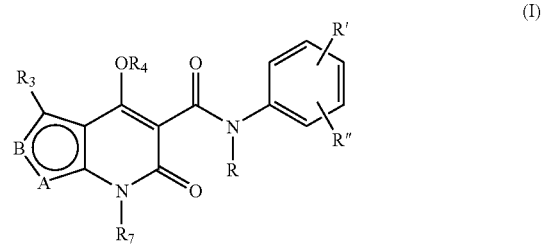

(I)

wherein
R is methyl, ethyl, n-propyl, iso-propyl, n-butyl or allyl;
R' is hydrogen, $C_1$-$C_4$ alkyl, $C_1$-$C_3$ alkoxy; halogen, trifluoromethyl or $OCH_xF_y$,
R" is hydrogen, fluoro or chloro, that R" being fluoro or chloro only when R' is fluoro or chloro;
$R_3$ is hydrogen or $C_1$-$C_5$ alkyl
$R_4$ is hydrogen, $CH_2OCOC(CH_3)_3$, pharmaceutically acceptable inorganic or organic cations, or $COR_4'$ wherein $R_4'$ is $C_1$-$C_5$ alkyl, phenyl, benzyl or phenethyl;
$R_7$ is methyl or ethyl;
one of A and B is sulphur and the other is C-$R_2$;
when A is S, $R_2$ is selected from hydrogen and methyl, with the proviso that $R_2$ is methyl only when $R_3$ is not hydrogen; and
when B is S, $R_2$ is hydrogen;
and any tautomer thereof.

A pharmaceutical composition comprising a compound of formula (I), a method of treating malignant tumours or diseases resulting from autoimmunity or pathologic inflammation.

21 Claims, No Drawings

COMPOUNDS

FIELD OF THE INVENTION

The present invention relates to substituted thieno[2,3-b]pyridine-5-carboxamide and 2-thia-4-aza-indene-6-carboxamide derivatives, to methods for their preparation, to compositions containing them, and to methods and use for clinical treatment of diseases resulting from autoimmunity and pathologic inflammation, and of malignant tumours. Examples of such autoimmune diseases are multiple sclerosis, insulin-dependent diabetes mellitus, systemic lupus erythematosus, rheumatoid arthritis, inflammatory bowel disease and psoriasis. Other diseases where inflammation plays a major role are diseases such as asthma, atherosclerosis, stroke and Alzheimer's disease. Furthermore, the types of solid tumours that are especially inhibited by the compounds of the-present invention include, for example, breast cancers, colon cancers, Kaposi's sarcoma, lung cancers, ovarian cancers, prostatic cancers, and skin cancers. More particularly, the present-invention relates to thieno[2,3-b]pyridine-5-carboxamide derivatives.

BACKGROUND OF THE INVENTION

Autoimmune diseases, e.g., multiple sclerosis (MS), insulin-dependent diabetes mellitus (IDDM), systemic lupus erythematosus (SLE), rheumatoid arthritis (RA), inflammatory bowel disease (IBD) and psoriasis represent assaults by the body's immune system which may be systemic in nature, or else directed at individual organs in the body. They appear to be diseases in which the immune system makes mistakes and, instead of mediating protective functions, becomes the aggressor (1).

MS is the most common acquired neurologic disease of young adults in Western Europe and North America. It accounts for more disability and financial loss, both in lost income and in medical care, than any other neurologic disease of this age group. There are approximately a total of 1,000,000 cases of MS in the United States and Europe.

Although the cause of MS is unknown, advances in brain imaging, immunology, and molecular biology have increased researchers' understanding of this disease. Several therapies are currently being used to treat MS, but no single treatment has demonstrated dramatic treatment efficacy. Current treatment of MS falls into three categories: treatment of acute exacerbations, modulation of progressive disease, and therapy for specific symptoms.

MS affects the central nervous system and involves a demyelination process, i.e., the myelin sheaths are lost whereas the axons are preserved. Myelin provides the isolating material that enables rapid nerve impulse conduction. Evidently, in demyelination, this property is lost. Although the pathogenic mechanisms responsible for MS are not understood, several lines of evidence indicate that demyelination has an immunopathologic basis. The pathologic lesions, the plaques, are characterised by infiltration of immunologically active cells such as macrophages and activated T cells (2).

In U.S. Pat. No. 5,219,864 some thieno[2,3-b]pyridine and thieno[3,2-b]pyridine derivatives represented by formula (A)

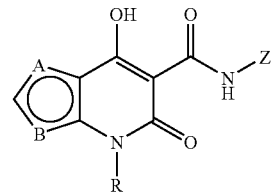

(A)

wherein Z represents pyridyl are claimed as immunoregulators and for the prevention and treatment of osteoporosis.

In WO 94/29295 compounds of general formula (B) are disclosed

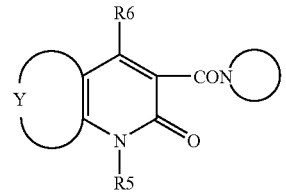

(B)

wherein Y among others represents

viz. thieno[3,2-b]pyridine derivatives, and N represents a bicyclic heterocyclic group containing at least one nitrogen atom, R5 represents lower alkyl and R6 represents hydroxy, and which possess immunomodulating activity, anti-inflammatory activity and anti-cancer activity.

DESCRIPTION OF THE INVENTION

A primary objective of the present invention is to provide novel thieno[2,3-b]pyridine-5-carboxamide and 2-thia-4-aza-indene-6-carboxamide derivatives, which by virtue of their pharmacological profile, with high potency in experimental models and low level of side-effects, are considered to be of value in the treatment of diseases resulting from autoimmunity and pathologic inflammation, and malignant tumours. The present invention relates to novel substituted thieno[2,3-b]pyridine-5-carboxamide derivatives and 2-thia-4-aza-indene-6-carboxamide derivatives, to methods for their preparation, to compositions containing them, and to methods and use for clinical treatment of diseases resulting from autoimmunity and pathologic inflammation, and of malignant tumours. Examples of such autoimmune diseases are multiple sclerosis, insulin-dependent diabetes mellitus, systemic lupus erythematosus, rheumatoid arthritis, inflammatory bowel disease and psoriasis, and other diseases where inflammation plays a major role are diseases such as asthma, atherosclerosis, stroke and Alzheimer's disease.

The types of solid tumours that are especially inhibited by the compounds of the present invention include, for example, breast cancers, colon cancers, Kaposi's sarcoma, lung cancers, ovarian cancers, prostatic cancers, and skin cancers. The approach we have chosen is to inhibit the tumour-induced angiogenesis and to stimulate the host immune system to evoke/enhance an antitumour response.

More particularly, the present invention relates to novel thieno[2,3-b]pyridine-5-carboxamide derivatives.

The term "treatment" as used herein includes prophylaxis, relieving the symptoms of disease, as well as curing the disease.

It has now surprisingly been found that the compounds of general formula (I)

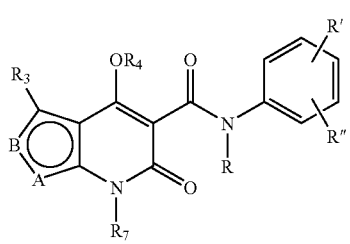

(I)

wherein

R is selected from methyl, ethyl, n-propyl, iso-propyl, n-butyl and allyl;

R' is selected from hydrogen, straight, branched or cyclic $C_1$-$C_4$ alkyl, preferably straight, branched or cyclic $C_1$-$C_3$ alkyl; straight, branched or cyclic $C_1$-$C_3$ alkoxy; fluoro, chloro, bromo, trifluoromethyl and $OCH_xF_y$, wherein x=0, 1, 2, y=1, 2, 3 with the proviso that x+y=3;

R" is selected from hydrogen, fluoro and chloro, with the proviso that R" is selected from fluoro and chloro only when R' is selected from fluoro and chloro;

$R_3$ is selected from hydrogen and straight, branched or cyclic $C_1$-$C_5$ alkyl, more preferably straight, branched or cyclic $C_1$-$C_4$ alkyl;

$R_4$ is selected from hydrogen, $CH_2OCOC(CH_3)_3$, pharmaceutically acceptable inorganic cations, such as lithium, sodium, potassium, magnesium, calcium, copper(II), zinc, aluminium and iron(III); organic cations, such as monoethanolamine and diethanolamine; and $COR_4'$ wherein $R_4'$ is selected from straight or branched $C_1$-$C_5$ alkyl, phenyl, benzyl, phenethyl and the like;

$R_7$ is selected from methyl and ethyl;

one of A and B is sulphur and the other is C—$R_2$;

when A is S, $R_2$ is selected from hydrogen and methyl, with the proviso that $R_2$ is methyl only when $R_3$ is not hydrogen; and when B is S, $R_2$ is hydrogen;

and any tautomer thereof, are unexpectedly effective in the treatment of individuals suffering from autoimmune and inflammatory diseases, and malignant tumours.

In the above formula (I), when A is sulphur, the ring

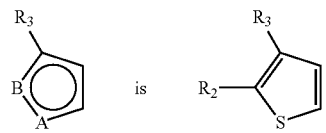

i.e. the compound is a thieno[2,3-b]pyridine derivative; and when B is sulphur, the ring

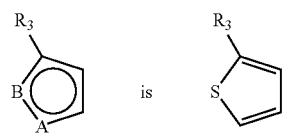

($R_2$ is hydrogen) i.e. the compound is a 2-thia-4-aza-indene derivative.

The compounds of general formula (I) may exist in different tautomeric forms and all such forms where such forms exist are included herein.

In a preferred embodiment of the invention
A is sulphur,
R is selected from methyl and ethyl,
R' is selected from para-methoxy, para-fluoro, para-chloro, para-trifluoromethyl and para-trifluoromethoxy when R" is hydrogen,
R" is ortho-fluoro provided that R' is para- or meta'-fluoro,
$R_2$ is hydrogen,
$R_3$ is selected from methyl, ethyl and iso-propyl, and
$R_7$ is methyl.

In another preferred embodiment of the invention
B is sulphur,
R is selected from methyl and ethyl,
R' is selected from para-methoxy, para-fluoro, para-chloro, para-trifluoromethyl and para-trifluoromethoxy when R" is hydrogen,
R" is ortho-fluoro provided that R' is para- or meta'-fluoro,
$R_3$ is selected from methyl, ethyl and iso-propyl, and
$R_7$ is methyl.

Preferred embodiments of the invention are those compounds represented by formula (Ia) in Table 1.

TABLE 1

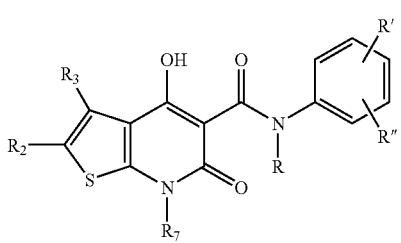

(Ia)

| Cpd | $R_2$ | $R_3$ | $R_7$ | R | R' | R" |
|---|---|---|---|---|---|---|
| #1 | H | $CH_3$ | $CH_3$ | $CH_3$ | H | H |
| #2 | H | $CH_3$ | $CH_3$ | $C_2H_5$ | H | H |
| #3 | H | $C_2H_5$ | $CH_3$ | $CH_3$ | H | H |
| #4 | H | iso-$C_3H_7$ | $CH_3$ | $CH_3$ | H | H |
| #5 | H | $CH_3$ | $CH_3$ | $CH_3$ | p-$CH_3$ | H |
| #6 | H | $CH_3$ | $CH_3$ | $CH_3$ | p-$OCH_3$ | H |

TABLE 1-continued

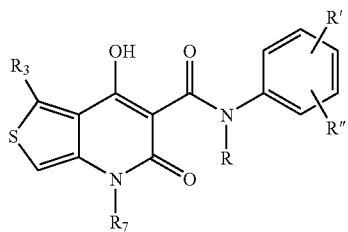

(Ia)

| Cpd | $R_2$ | $R_3$ | $R_7$ | R | R' | R" |
|---|---|---|---|---|---|---|
| #7 | H | $CH_3$ | $CH_3$ | $CH_3$ | p-Cl | H |
| #8 | H | $CH_3$ | $CH_3$ | $CH_3$ | p-F | o-F |
| #9 | H | $CH_3$ | $CH_3$ | $CH_3$ | p-$OCF_3$ | H |

Another preferred embodiment of the invention is compound (Ib)

(Ib)

wherein $R_3$ and $R_7$ are methyl, R is methyl or ethyl, and R' and R" are hydrogen. In a preferred compound (compound #10) R is methyl.

Several spontaneously occurring autoimmune diseases in man have experimental models that are spontaneously occurring in certain strains of laboratory animals or can be induced in laboratory animals by immunization with specific antigen(s) from the target organ.

Experimental autoimmune encephalomyelitis (EAE) as a model for autoimmune inflammatory diseases of the central nervous system (CNS) has been the most widely used model for the human disease multiple sclerosis.

Autoimmunity to type II collagen can experimentally be induced in certain strains of mice or rats and may lead to the development of polyarthritis. The collagen induced arthritis has several features in common with the human disorder rheumatoid arthritis.

The compounds of general formula (I) as well as some prior art/reference compounds were assayed for inhibition of acute experimental autoimmune encephalomyclitis (aEAE) in mice. Surprising and unexpected results were obtained when comparing reference thieno[3,2-b]pyridine-6-carboxamide derivatives with the corresponding thieno[2,3-b]pyridine-5-carboxamide and 2-thia-4-aza-indene-6-carboxamide derivatives of the present invention. The thieno[2,3-b]pyridine-5-carboxamide and 2-thia-4-aza-indene-6-carboxamide derivatives of the invention turned out clearly superior. In contrast to the compounds of the invention, e.g. 6,7-dihydro-N,7-dimethyl-4-hydroxy-N-phenyl-6-oxo-thieno[2,3-b]pyridine-5-carboxamide and 4,5-dihydro-N,4-dimethyl-7-hydroxy-N-phenyl-5-oxo-2-thia-4-aza-indene-6-carboxamide, the reference compound 4,5-dihydro-N,4-dimethyl-7-hydroxy-N-phenyl-5-oxo-thieno[3,2-b]pyridine-6-carboxamide turned out inactive in the aEAE model. Likewise, an N-phenyl group in exchange for an N-pyridyl group in the carboxamide moiety resulted in superior activity Hence, the reference compound 6,7-dihydro-4-hydroxy-N-(3-pyridyl)-N,3,7-trimethyl-6-oxo-thieno[2,3-b]pyridine-5-carboxamide turned out poorly active in comparison with the inventive compound 6,7-dihydrohydroxy-N-phenyl-N,3,7-trimethyl-6-oxo-thieno[2,3-b]pyridine-5-carboxamide. The prior art compound 6,7-dihydro-4-hydroxy-N-(3-pyridyl)-6-oxo-thieno[2,3-b]pyridine-5-carboxamide, disclosed in U.S. Pat. No. 5,219,864, turned out inactive.

All embodiments of the invention as disclosed in the claims are herewith included in the specification.

The compounds of general formula (I) may be prepared by methods known in the literature and by the following methods:

Method A:

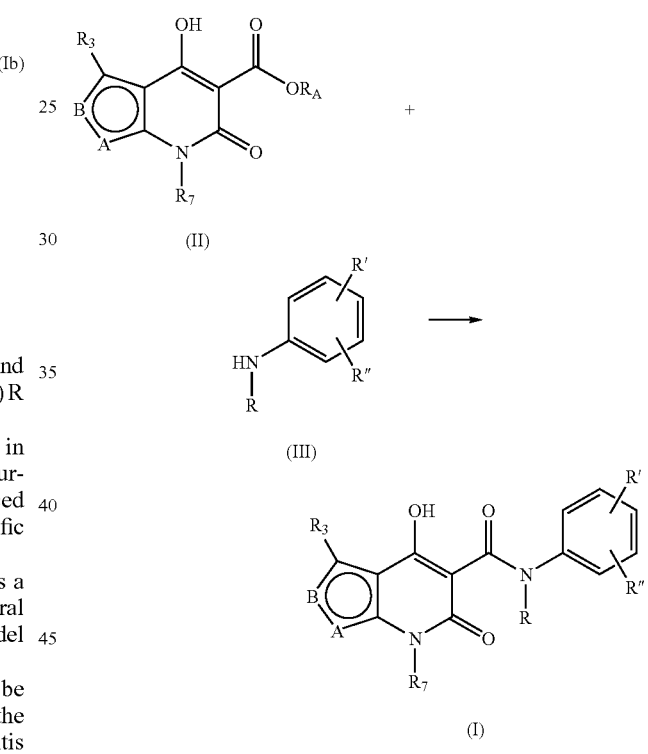

The compounds of general formula (I) may be prepared by known methods and, for example, as shown above, by reaction of a carboxylic acid ester derivative (II; $R_A$=alkyl group of 1-4 carbons) with an aniline in a suitable solvent, e.g. an aliphatic hydrocarbon such as heptane, octane and the like or an aromatic hydrocarbon such as toluene, xylene and the like. General methods for preparation of the carboxylic acid ester derivatives of formula (II) are described below starting from a 2-aminothiophene-3-carboxylate or a 4-aminothiophene-3-carboxylate. The aminothiophene-3-carboxylates are commercially available or known from literature (3, 4, 5, 6, 7). N-alkylated anilines of formula (III) are commercially available or known from literature (8). New aminothiophene-3-carboxylates and N-alkylated anilines of formula (III) may be prepared by methods, which are generally analogous to those of said literature.

Method B:

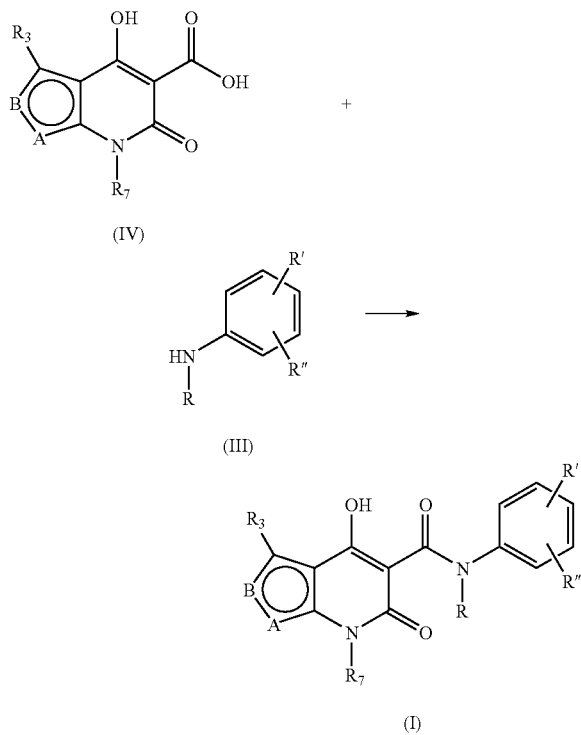

The compounds of formula (I) may also be prepared by reaction of a compound of formula (IV) with an aniline of formula (III). Various coupling reagents known in the art may be used, e.g., carbodiimides known from literature in U.S. Pat. No. 4,547,511. One suitable coupling method utilizes thionyl chloride in the presence of triethylamine and a suitable solvent such as dichloromethane. This method may be used in instances when direct coupling between ester and aniline does not work, e.g., when the aniline contains electron-withdrawing substituents. The carboxylic acid derivatives of formula (IV) may be obtained from the corresponding esters of formula (II) by acidic cleavage as described below.

The following examples are intended to illustrate the invention without restricting the scope thereof.

EXAMPLE 1

6,7-Dihydro-3,7-dimethyl-4-hydroxy-6-oxo-thieno[2,3-b]pyridine-5-carboxylic acid ethyl ester (Intermediate)

Ethyl 2-amino-4-methyl-thiophene-3-carboxylate, (27.0 mmol, 5.0 g), was heated in diethyl malonate (25 ml) at 180° C. for 3 hrs, and the formed ethanol was allowed to distil off. The oil bath temperature was lowered and diethyl malonate was distilled off at reduced pressure to give the intermediate malonic amide, 2-(2-ethoxycarbonyl-acetylamino)-4-methyl-thiophene-3-carboxylic acid ethyl ester, as an oil that slowly crystallized upon standing (7.7 g, 95%). The malonic amide was dissolved in N,N-dimethylacetamide, (DMA, 40 ml), and sodium hydride (NaH 80%, 2.0 equiv. 54 mmol, 1.62 g) was added. The mixture was heated at 60° C. for 1 h. After cooling and addition of water (300 ml), the product was precipitated by addition of concentrated hydrochloric acid (HCl) to pH 1.5. The precipitate was collected by filtration and recrystallized from methyl isobutyl ketone giving 6,7-dihydro-4-hydroxy-3-methyl-6-oxo-thieno[2,3-b]pyridine-5-carboxylic acid ethyl ester (3.8 g, 56%). The carboxylic acid ethyl ester, (11.9 mmol, 3.02 g), was dissolved in DMA (40 ml) and NaH (2.1 equiv., 25 mmol, 750 mg) was added. The mixture was heated to 40° C. for 10 min. Thereafter it was cooled to 10° C. and dimethyl sulphate (1.2 equiv., 14.3 mmol, 1.37 ml) was added. The mixture was stirred at ambient temperature for 1 h and then cooled on an ice bath. Water (200 ml) was added and the mixture was acidified with 5 M HCl to pH 1.5. The precipitate was collected and recrystallized from toluene/heptane giving the title compound (2.4 g, 75%).

$^1$H NMR (CDCl$_3$): δ 1.45 (3H, t), 2.48 (3H, d), 3.55 (3H, s), 4.45 (2H, q), 6.46 (1H, q broad), 14.22 (1H, s).

In essentially the same manner the following compounds were obtained from the corresponding starting materials:

6,7-dihydro-4-hydroxy-2,3,7-trimethyl-6-oxo-thieno[2,3-b]pyridine-5-carboxylic acid methyl ester;

6,7-dihydro-3-ethyl-4-hydroxy-7-methyl-6-oxo-thieno[2,3-b]pyridine-5-carboxylic acid methyl ester;

6,7-dihydro-4-hydroxy-3-isopropyl-7-methyl-6-oxo-thieno[2,3-b]pyridine-5-carboxylic acid methyl ester;

6,7-dihydro-4-hydroxy-7-methyl-6-oxo-thieno[2,3-b]pyridine-5-carboxylic acid methyl ester;

6,7-dihydro-2,7-dimethyl-4-hydroxy-6-oxo-thieno[2,3-b]pyridine-5-carboxylic acid methyl ester;

6,7-dihydro-3-(4-fluorophenyl)-4-hydroxy-7-methyl-6-oxo-thieno[2,3-b]pyridine-5-carboxylic acid ethyl ester; and 4,5-dihydro-7-hydroxy-4-methyl-5-oxo-2-thia-4-aza-indene-6-carboxylic acid methyl ester.

EXAMPLE 2

4,5-Dihydro-1,4-dimethyl-7-hydroxy-5-oxo-2-thia-4-aza-indene-6-carboxylic acid ethyl ester (Intermediate)

Ethyl 4-amino-2-methyl-thiophene-3-carboxylate (12.8 mmol, 2.37 g) was dissolved in 1,4-dioxane (20 ml) and ethyl malonyl chloride (90%) (19.2 mmol, 2.73 ml) was added. The reaction mixture was heated at 50° C. for 1 h and was then allowed to reach room temperature. The reaction mixture was poured onto ice (60 g) and the product was collected by filtration, washed with water and dried (3.32 g, 87%). The malonic amide was dissolved in N,N-dimethylacetamide (DMA, 35 ml) and sodium hydride (NaH 60%, 2.0 equiv., 22.1 mmol) was added. The reaction mixture was heated at 60° C. for 1 h. After cooling and addition of water (50 ml) the product was precipitated by addition of 1 M hydrochloric acid (HCl, aq.) (30 ml). The precipitate was collected by filtration and was re-crystallized from ethanol giving 4,5-dihydro-7-hydroxy-1-methyl-5-oxo-2-thia-4-aza-indene-6-carboxylic acid ethyl ester (1.46 g, 52%). The carboxylic acid ethyl ester was dissolved in dimethylformamide (DMA, 40 ml) and NaH (3.0 equiv., 17.3 mmol, 692 mg) was added. The reaction mixture was heated to 40° C. for 15 minutes and was then cooled to 10° C. Iodomethane (1.3 equiv., 7.49 mmol, 0.47 ml) was added, the reaction mixture was stirred at ambient temperature for 2 hrs and was then poured onto 0.5 M HCl (aq) (50 ml). The precipitate was collected by filtration and re-crystallized from ethanol and then again from methyl isobutyl ketone to give the title compound (524 mg, 89%).

$^1$H NMR(NaOD/D$_2$O): δ 1.28 (3H, t), 2.79 (3H, s), 3.82 (3H, s), 4.30 (2H, q), 6.81 (1H, s).

In essentially the same manner the following compounds were obtained from the corresponding starting materials:

6,7-dihydro-3-ethyl-4-hydroxy-7-methyl-6-oxo-thieno[2,3-b]pyridine-5-carboxylic acid methyl ester;
6,7-dihydro-4-hydroxy-7-methyl-3-tert-butyl-6-oxo-thieno[2,3-b]pyridine-5-carboxylic acid methyl ester;
6,7-dihydro-4-hydroxy-3-isobutyl-7-methyl-6-oxo-thieno[2,3-b]pyridine-5-carboxylic acid methyl ester;
6,7-dihydro-3-(2,2-dimethyl-propyl)-4-hydroxy-7-methyl-6-oxo-thieno[2,3-b]pyridine-5-carboxylic acid methyl ester;
6,7-dihydro-3-(1-ethylpropyl)-4-hydroxy-7-methyl-6-oxo-thieno[2,3-b]pyridine-5-carboxylic acid methyl ester;
3-cyclohexyl-6,7-dihydro-4-hydroxy-7-methyl-6-oxo-thieno[2,3-b]pyridine-5-carboxylic acid methyl ester; and
4,5-dihydro-3,4-dimethyl-7-hydroxy-5-oxo-2-thia-4-aza-indene-6-carboxylic acid methyl ester.

EXAMPLE 3

4,5-Dihydro-7-hydroxy-4-methyl-5-oxo-thieno[3,2-b]pyridine-6-carboxylic acid ethyl ester (Not According to the Invention)

A mixture of methyl 3-aminothiophene-2-carboxylate (63 mmol, 10.0 g) and ethyl chloroformate (50 ml) was refluxed for 2 hrs and then evaporated to dryness. The residue was dissolved in ethanol (130 ml) and sodium hydroxide (NaOH, 65 mmol, 3.84 g) in water (35 ml) was added. After stirring at room temperature for 48 hrs the mixture was acidified with 1M HCl and diluted with water. The precipitate was collected, washed with water, dried under vacuum and recrystallized from toluene/heptane resulting in 3-ethoxycarbonylamino-thiophene-2-carboxylic acid, (10.2 g, 73%). This acid, (23.2 nanol, 5.0 g), and phosphorus tribromide (12 mmol, 1.14 ml) were dissolved in 1,4-dioxane (50 ml). The mixture was stirred at 100° C. for 2 hrs and then cooled before it was concentrated on a rotary evaporator. The precipitate formed upon addition of toluene was isolated by filtration giving 1H-thieno[3,2-d][1,3]oxazine-2,4-dione (3.96. g, 100%). This intermediate (20.6 mmol, 3.5 g) was dissolved in DMA (40 ml) and cooled on an ice-bath. NaH (22.7 mmol, 780 mg) was added followed by addition of methyl iodide (25 mmol, 1.6 ml). The mixture was stirred at room temperature overnight and then diethyl malonate (25 mmol, 3.85 ml) and NaH (22.7 mmol, 780 mg) were added. After the addition the mixture was heated at 85° C. for 2 hrs and then the mixture was cooled. Water was added and the mixture was acidified with 1 M HCl and extracted with chloroform. The extract was dried, concentrated, and chromatographed (SiO$_2$, chloroform/methanol/acetic acid; 40/1/0.1) to yield the title compound (1.4 g, 26%).

$^1$H NMR (CDCl$_3$): δ 1.45 (3H, t), 3.61 (3H, s), 4.45 (2H, q), 7.00 (1H, d), 7.76 (1H, d), 13.92 (1H, s broad).

EXAMPLE 4

6,7-Dihydro-3,7-dimethyl-4-hydroxy-6-oxo-thieno[2,3-b]pyridine-5-carboxylic acid (Intermediate)

6,7-Dihydro-3,7-dimethyl-4-hydroxy-6-oxo-thieno[2,3-b]pyridine-5-carboxylic acid ethyl ester (5.72 mmol, 1.45 g) was heated at 55° C. in 33% hydrobromic acid/acetic acid, (35 mmol HBr, 6.0 ml). After 2 hrs the mixture was cooled and 2-propanol (30 ml) was added. The precipitate was collected by filtration and dried in vacuum to yield the title compound (1.28 g, 93%).

$^1$H NMR (CDCl$_3$): δ 2.53 (3H, d), 3.67 (3H, s), 6.63 (1H, q broad), 14.48 (1H, s), 15.29 (1H, s).

In essentially the same manner the following compounds were obtained from the corresponding starting materials:

6,7-dihydro-2,7-dimethyl-4-hydroxy-6-oxo-thieno[2,3-b]pyridine-5-carboxylic acid;
6,7-dihydro-4-hydroxy-2,3,7-trimethyl-6-oxo-thieno[2,3-b]pyridine-5-carboxylic acid,
6,7-dihydro-2,7-dimethyl-3-ethyl-4-hydroxy-6-oxo-thieno[2,3-b]pyridine-5-carboxylic acid;
4,5-dihydro-7-hydroxy-4-methyl-5-oxo-2-thia-4-aza-indene-6-carboxylic acid; and
4,5-dihydro-7-hydroxy-4-methyl-5-oxo-thieno[3,2-b]pyridine-6-carboxylic acid.

EXAMPLE 5

6,7-Dihydro-4-hydroxy-N-(4-methoxyphenyl)-N,3,7-trimethyl-6-oxo-thieno[2,3-b]pyridine-5-carboxamide (Method A)

6,7-Dihydro-3,7-dimethyl-4-hydroxy-6-oxo-thieno[2,3-b]pyridine-5-carboxylic acid ethyl ester (3.74 mmol, 1.0 g), N-methyl-p-anisidine, (3 equiv., 11.2 mmol, 1.57 g), and n-octane (60 ml) were heated to the boiling point under nitrogen on an oil bath. The volatiles, (approximately 40 ml) were allowed to distil off during 6 hrs and the remaining n-octane was removed using a rotary evaporator. The residue was dissolved in chloroform and washed with cold 1M sulphuric acid. The organic phase was extracted with 0.5 M NaOH and pH in the aqueous phase was adjusted to approximately 6.5. The cloudy solution was filtered through celite. Methanol (corresponding to 10% of the volume) was added, and the clear solution was then acidified with 1 M HCl to pH 1.5. The resulting precipitate was left overnight, collected by filtration and dried in vacuum giving the title compound (1.06 g, 79%).

$^1$H NMR (CDCl$_3$): δ 2.51 (3H, d), 3.29 (3H, s broad), 3.43 (3H, s), 3.78 (3H, s), 6.45 (1H, q broad), 6.79 (2H, d broad), 7.12 (2H, d broad), 12.60 (1H, s broad).

In essentially the same manner the following compounds were obtained from the corresponding starting materials:

6,7-dihydro-N,7-dimethyl-4-hydroxy-N-phenyl-6-oxo-thieno[2,3-b]pyridine-5-carboxamide, yield 53%.

$^1$H NMR (CDCl$_3$): δ 3.27 (3H, s broad), 3.48 (3H, s), 6.88 (1H, d), 7.15-7.22 (3H, m), 7.27 (2H, t broad), 7.32 (2H, d), 12.50 (1H, s broad).

6,7-dihydro-N,7-dimethyl-3-ethyl-4-hydroxy-N-phenyl-6-oxo-thieno[2,3-b]pyridine-5-carboxamide, yield 86%.

$^1$H NMR (CDCl$_3$): δ 1.31 (3H, t), 2.98 (2H, q), 3.26 (3H, s broad), 3.48 (3H, s), 6.48 (1H, s), 7.14-7.30 (5H, m), 12.78 (1H, s).

6,7-dihydro-N,7-dimethyl-4-hydroxy-3-iso-propyl-N-phenyl-6-oxo-thieno[2,3-b]pyridine-5-carboxamide, yield 66%.

$^1$H NMR (CDCl$_3$): δ 1.28 (6H, d), 3.24 (3H, s broad), 3.47 (3H, s), 3.57-3.68 (1H, m), 6.52 (1H, s), 7.12-7.20 (3H, m), 7.23-7.29 (2H, m), 12.94 (1H s broad).

6,7-dihydro-N,7-dimethyl-4-hydroxy-3-iso-butyl-N-phenyl-6-oxo-thieno[2,3-b]pyridine-5-carboxamide, yield 76%.

$^1$H NMR (CDCl$_3$): δ 0.97 (6H, d), 2.04 (1H, m), 2.77 (2H, d), 3.28 (3H,s broad), 3.50 (3H, s), 6.47 (1H, s), 7.17-7.32 (5H, m), 12.85 (1H, s).

6,7-dihydro-N,7-dimethyl-4-hydroxy-N-phenyl-3-tert-butyl-6-oxo-thieno[2,3-b]pyridine-5-carboxamide, yield 83%.

¹H NMR (CDCl₃): δ 1.47 (9H, s), 3.28 (3H, s), 3.49 (3H, s), 6.61 (1H, s), 7.15-7.32 (5H, m), 13.60 (1H, s).

6,7-dihydro-N,7-dimethyl-3-(1-ethyl-propyl)-4-hydroxy-N-phenyl-6-oxo-thieno[2,3-b]pyridine-5-carboxamide, yield: 23%.

¹H NMR (CDCl3): δ 0.89 (6H, t), 1.69 (4H, m), 3.27 (3H, bs), 3.44 (1H, bs), 3.48 (3H, s), 6.48 (1H, s), 7.18 (3H, m), 7.28 (2H, m), 12.97 (1H, bs).

6,7-dihydro-N,7-dimethyl-3-(2,2-dimethyl-propyl)-4-hydroxy-N-phenyl-6-oxo-thieno[2,3-b]pyridine-5-carboxamide, yield 63%; not included in the claims.

¹H NMR (CDCl₃): δ 0.98 (9H, s), 2.96 (2H, s), 3.29 (3H, s broad), 3.51 (3H, s), 6.48 (1H, s), 7.17-7.33 (5H, m), 12.85 (1H, s).

3-cyclohexyl-6,7-dihydro-N,7-diethyl-4-hydroxy-N-phenyl-6-oxo-thieno[2,3-b]pyridine-5-carboxamide, yield 60%; not included in the claims.

¹H NMR (CDCl₃): δ 1.22-2.18 (10H, m, cyclohexyl-CH₂), 3.30 (4H, broad signal, N-Me and cyclohexyl-CH), 3.50 (3H, s), 6.52 (1H, s), 7.17-7.32 (5H, m), 12.95 (1H, s).

6,7-dihydro-3,7-dimethyl-N-ethyl-4-hydroxy-N-phenyl-6-oxo-thieno[2,3-b]pyridine-5-carboxamide, yield 87%.

¹H NMR (DMSO-d₆): δ 1.01 (3H, t), 2.31 (3H, s), 3.29 (3H, s), 3.74 (2H, q broad), 6.72 (1H, s broad), 7.10-7.31 (5H, m), 11.0 (1H, s broad).

N,3-diethyl-6,7-dihydro-4-hydroxy-7-methyl-N-phenyl-6-oxo-thieno[2,3-b]pyridine-5-carboxamide yield 76%.

¹H-NMR (CDCl₃) δ 1.20 (3H, t), 1.30 (3H, t), 2.97 (2H, q), 3.19 (3H, s), 6.47 (1H, s), 7.15 (3H, t), 7.24 (2H, t), 12.83 (1H, bs).

6,7-dihydro-N-ethyl-4-hydroxy-3-iso-propyl-7-methyl-N-phenyl-6-oxo-thieno[2,3-b]pyridine-5-carboxamide, yield 67%.

¹H-NMR (CDCl₃) δ 1.21 (3H, t), 1.30 (6H, d), 3.19 (3H, s), 3.64 (1H, m), 3.97 (2H, q), 6.51 (1H, s), 7.15 (3H, t), 7.24 (2H, m), 12.98 (1H, bs).

6,7-dihydro-3,7-dimethyl-4-hydroxy-N-phenyl-N-propyl-6-oxo-thieno[2,3-b]pyridine-5-carboxamide, yield 58%.

¹H-NMR (CDCl₃) δ 0.92 (3H, t), 1.63 (2H, m), 2.52 (3H, d), 3.17 (3H, s), 3.87 (2H, t), 6.43 (1H, d), 7.14 (3H, t), 7.23 (2H, t), 12.62 (1H, bs).

6,7-dihydro-N,3-dimethyl-7-ethyl-4-hydroxy-N-phenyl-6-oxo-thieno[2,3-b]pyridine-5-carboxamide pyrrolidine salt, yield 75%.

¹H NMR (CDCl₃): δ 1.08 (3H, broad signal), 1.79 (4H, m), 2.45 (3H, s), 2.98 (4H, m), 3.35 (3H, s), 3.85 (2H, broad signal), 6.25 (1H, s broad), 7.08-7.36 (5H, m).

6,7-dihydro-4-hydroxy-N-(4-methylphenyl)-N,3,7-trimethyl-6-oxo-thieno[2,3-b]pyridine-5-carboxamide, yield 81%.

¹H NMR (CDCl₃): δ 2.29 (3H, s), 2.50 (3H, d), 3.26 (3H, s broad), 3.43 (3H, s), 6.43 (1H, q broad), 7.06 (4H, s), 12.70 (1H, s broad).

6,7-dihydro-4-hydroxy-N-(4-iso-propylphenyl)-N,3,7-trimethyl-6-oxo-thieno[2,3-b]pyridine-5-carboxamide, yield 85%.

¹H NMR (CDCl₃): δ 1.22 (6H, d), 2.53 (3H, s), 2.88 (1H, m), 3.25 (3H, s broad), 3.46 (3H, s), 6.45 (1H, s broad), 7.07-7.17 (4H, m), 12.8 (1H, s).

6,7-dihydro-4-hydroxy-N-(4-trifluoromethylphenyl)-N,3,7-trimethyl-6-oxo-thieno[2,3-b]pyridine-5-carboxamide, yield 76%.

¹H NMR (CDCl₃): δ 2.52 (3H, s), 3.23 (3H, s), 3.47 (3H, s), 6.47 (1H, s broad), 7.12 (2H, d), 7.22 (2H, d), 12.70(1H, s).

6,7-dihydro-N,7-dimethyl-4-hydroxy-3-ethyl-N-(4-methoxyphenyl)-6-oxo-thieno[2,3-b]pyridine-5-carboxamide, yield 67%.

¹H-NMR (CDCl₃) δ 1.29 (3H, t), 2.96 (2H, d), 3.29 (3H, bs), 3.43 (3H, s), 3.77(3H, s), 6.48 (1H, s), 6.79 (2H, d), 7.11 (2H, d), 12.69 (1H, bs).

N-(4-chlorophenyl)-6,7-dihydro-3,7-dimethyl-N-ethyl-4-hydroxy-6-oxo-thieno[2,3-b]pyridine-5-carboxamide, yield 54%.

¹H-NMR (CDCl₃) δ 1.19 (3H, t), 2.51 (3H, d), 3.23 (3H, s), 3.93 (2H, q), 6.45 (1H, d), 7.09 (2H, d), 7.21 (2H, d), 12.73 (1H, bs).

N-(4-chorophenyl)-6,7-dihydro-N,7-dimethyl-3-yl-4-hydroxy-6-oxo-thieno[2,3-b]pyridine-5-carboxamide, yield 57%.

¹H-NMR (CDCl₃) δ 1.29 (3H, t), 2.96 (2H, q), 3.28 (3H, s), 3.45 (3H, s), 6.50 (1H, s), 7.13 (2H, d), 7.23 (2H, d), 12.79 (1H, bs).

N-(2,4-difluorophenyl)-6,7-dihydro-N,7-dimethyl-3-ethyl-4-hydroxy-6-oxo-thieno[2,3-b]pyridine-5-carboxamide, yield 44%.

¹H-NMR (CDCl₃) δ 1.29 (3H, t), 2.96 (2H, q), 3.25 (3H, bs), 3.38 (3H, s), 6.49 (1H, s), 6.69 (1H, bs), 6.86 (1H, bt), 7.05 (1H, bs), 12.72 (1H, bs).

N-(2,4-difluorophenyl)-6,7-dihydro-4-hydroxy-3-iso-propyl-N,7-dimethyl-6-oxo-thieno[2,3-b]pyridine-5-carboxamide, yield 37%.

¹H-NMR (CDCl₃) δ 1.29 (6H, d), 3.25 (3H, bs), 3.38 (3H, s), 3.62 (1H, m), 6.54 (1H, s), 6.71 (1H, bs), 6.87 (1H, bt), 7.05 (1H, bs), 12.85 (1H, bs).

6,7-dihydro-N,7-dimethyl-3-(4-fluorophenyl)-4-hydroxy-N-phenyl-6-oxo-thieno[2,3-b]pyridine-5-carboxamide, yield 92%; not included in the claims.

¹H NMR (CDCl₃): δ 3.30 (3H, s broad), 3.44 (3H, s), 6.68 (1H, s), 7.04-7.11 (2H, m), 7.14-7.20 (3H, m), 7.23-7.30 (2H, m), 7.42-7.49 (2H, m), 12.67 (1H s broad)

4,5-dihydro-7-hydroxy-N-phenyl-N,1,4-trimethyl-5-oxo-2-thia-4-aza-indene-6-carboxamide, yield 87%.

¹H NMR (CDCl₃): δ 2.86 (3H, s), 3.21 (3H, s broad), 3.48 (3H, s), 6.17 (1H, s), 7.13-7.32 (5H, m), 12.89 (1H, s broad).

4,5-dihydro-1,4-dimethyl-N-ethyl-7-hydroxy-N-phenyl-5-oxo-2-thia-4-aza-indene-6-carboxamide, yield 76%.

¹H-NMR (CDCl₃) δ 1.20 (3H, t), 2.86 (3H, s), 3.04 (3H, s), 3.97 (2H, q), 6.14 (1H, s); 7.15 (3H, m), 7.24 (2H, m), 12.93 (1H, bs).

4,5-dihydro-7-hydroxy-N-(4-methylphenyl)-N,1,4-trimethyl-5-oxo-2-thia-4-aza-indene-6-carboxamide, yield 68%.

¹H-NMR (CDCl₃) δ 2.30 (3H, s), 2.85 (3H, s), 3.13 (3H, bs), 3.44 (3H, s), 6.18 (1H, s), 7.07 (4H, bs), 12.88 (1H, bs).

4,5-dihydro-7-hydroxy-N-(4-methoxyphenyl)-N,1,4-trimethyl-5-oxo-2-thia-4-aza-indene-6-carboxamide, yield 55%.

¹H-NMR (CDCl₃) δ 2.85 (3H, s), 3.14 (3H, bs), 3.78 (3H, s), 6.18 (1H, s), 6.80 (2H, bd), 7.11 (2H, bd), 12.79 (1H, bs).

N-(4-chlorophenyl)-4,5-dihydro-7-hydroxy-N,1,4-trimethyl-5-oxo-2-thia-4-aza-indene-6-carboxamide, yield 50%.

¹H-NMR (CDCl₃) δ 2.86 (3H, s), 3.14 (3H, s), 3.44 (3H, s), 6.20 (1H, s), 7.12 (2H, d), 7.23 (2H, d), 12.87 (1H, bs).

N-(2,4-difluorophenyl)-4,5-dihydro-7-hydroxy-N,1,4-trimethyl-5-oxo-2-thia-4-aza-indene-6-carboxamide, yield 14%.

¹H-NMR (CDCl₃) δ 2.85 (3H, s), 3.09 (3H, bs), 3.37 (3H, s), 6.18 (1H, bs), 6.70 (1H, bs), 6.86 (1H, bt), 7.05 (1H, bs), 12.83 (1H, bs).

N-(2,5-difluorophenyl)-4,5-dihydro-7-hydroxy-N,1,4-trimethyl-5-oxo-2-thia-4-aza-indene-6-carboxamide, yield 48%.

¹H-NMR (CDCl₃) δ 2.86 (3H, s), 3.15 (3H, bs), 3.39 (3H, s), 6.19 (1H, s), 6.88 (2H, m), 7.06 (1H,dt), 12.89 (1H, bs).
4,5-dihydro-7-hydroxy-N-(4-trifluoromethylphenyl)-N,1,4-trimethyl-5-oxo-2-thia-4-aza-indene-6-carboxamide, yield 36%.
¹H-NMR (CDCl₃) δ 2.87 (3H, s), 3.08 (3H, s), 3.50 (3H, s), 6.21 (1H, s), 7.30 (2H, d), 7.52 (2H, d) 12.98 (1H, bs).
4,5-dihydro-7-hydroxy-N-(4-trifluoromethylphenyl)-N,1,4-trimethyl-5-oxo-2-thia-4-aza-indene-6-carboxamide, yield 52%.
¹H-NMR (CDCl₃) δ 2.86 (3H, s), 3.09 (3H, s), 3.46 (3H, s), 6.19 (1H, s), 7.11 (2H, d), 7.21 (2H, d), 12.87 (1H, bs).

EXAMPLE 6

N-(2,5-Difluorophenyl)-6,7-dihydro-4-hydroxy-N,3,7-trimethyl-6-oxo-thieno[2,3-b]pyridine-5-carboxamide (Method B)

To 6,7-dihydro-3,7-dimethyl-4-hydroxy-6-oxo-thieno[2,3-b]pyridine-5-carboxylic acid (4.18. mmol, 1.0 g) in dichloromethane (10 ml), triethylamine (4 equiv., 16.7 mmol, 2.4 ml) and N-methyl-2,5-difluoroaniline (1.2 equiv., 5.0 mmol, 720 mg) were added. To the mixture stirred under nitrogen and cooled to 0° C., a solution of thionyl chloride (1.3 equiv., 5.4 mmol, 0.4 ml) in dichloromethane (5 ml) then was added during 30 min. The stirring was continued at 0° C. for 1 h and then at room temperature for another 20 min. The reaction mixture was diluted with chloroform and quickly washed with cold 1M sulphuric acid. The organic phase then was immediately extracted with 0.5 M NaOH. Remaining traces of chlorinated organic solvents were removed using a rotary evaporator. The pH was adjusted to just above the point where the desired product starts to precipitate (approximately pH 6.5) and the solution was filtered through celite. The product was precipitated by acidification with 1 M HCl until pH was approximately 1-2 and the mixture was allowed to stand for 2 hrs. The resulting precipitate was collected by filtration, washed with water, and dried under reduced pressure to give the title compound (1.26 g, 83%).
¹H NMR (CDCl₃): δ 2.53 (3H, d), 3.31 (3H, s broad), 3.42 (3H, s), 6.49 (1H, q broad), 6.84-6.95 (2H, m), 7.05-7.12 (1H, m), 12.73 (1H, s broad).

In essentially the same manner the following compounds were obtained from the corresponding starting materials:
6,7-dihydro-4-hydroxy-N-phenyl-N,3,7-trimethyl-6-oxo-thieno[2,3-b]pyridine-5-carboxamide, yield 81%.
¹H NMR (CDCl₃): δ 2.50 (3H, d), 3.23 (3H, s broad), 3.46 (3H, s), 6.42 (1H, q), 7.12-7.19 (3H, m), 7.21-7.27 (2H, m), 12.65 (1H, s broad).
6,7-dihydro-4-hydroxy-N-phenyl-N,2,3,7-tetramethyl-6-oxo-thieno[2,3-b]pyridine-5-carboxamide, yield 75%.
¹H NMR(CDCl₃): δ 2.32 (3H, s), 2.40 (3H, s), 3.21 (3H, s broad), 3.47 (3H, s), 7.14-7.29 (3H, m), 7.26 (2H, t broad), 12.60 (1H, s broad).
6,7-dihydro-3-ethyl-4-hydroxy-N-phenyl-N,2,7-trimethyl-6-oxo-thieno[2,3-b]pyridine-5-carboxamide, yield 87%.
¹H NMR (CDCl₃): δ 1.19 (3H, t), 2.34 (3H, s), 2.86 (2H, q), 3.22 (3H, s), 3.47 (3H, s), 7.14-7.22 (3H, m), 7.27 (2H, t broad), 12.75 (1H, s broad).
N-(4-chlorophenyl)-6,7-dihydro-4-hydroxy-N,3,7-trimethyl-6-oxo-thieno[2,3-b]pyridine-5-carboxamide, yield 90%.
¹H NMR (CDCl₃): δ 2.50 (3H, d), 3.26 (3H, s), 3.43 (3H, s), 6.45 (1H, q broad), 7.11 (2H, d), 7.21 (2H, d), 12.66 (1H, s broad).
N-(2,4-difluorophenyl)-6,7-dihydro-4-hydroxy-N,3,7-trimethyl-6-oxo-thieno[2,3-b]pyridine-5-carboxamide, yield 92%.
¹H NMR (CDCl₃): δ 2.51 (3H, d), 3.25 (3H, s broad), 3.38 (3H, s), 6.45 (1H, s), 6.70 (1H, s broad), 6.87 (1H, t broad), 7.04 (1H, s broad), 12.62 (1H, s broad).
6,7-dihydro-4-hydroxy-N-(4-trifluoromethylphenyl)-N,3,7-trimethyl-6-oxo-thieno[2,3-b]pyridine-5-carboxamide, yield 76%.
¹H NMR (CDCl₃): δ 2.52 (3H, d), 3.23 (3H, s), 3.50 (3H, s), 6.48 (1H, q broad), 7.31 (2H, d), 7.53 (2H, d) 12.76 (1H, s broad).
6,7-dihydro-3,7-dimethyl-N-ethyl-4-hydroxy-N-(4-trifluoromethylphenyl)-6-oxo-thieno[2,3-b]pyridine-5-carboxamide, yield 68%.
¹H NMR (CDCl₃): δ 1.21 (3H, t), 2.52 (3H, s), 3.18 (3H, s), 3.99 (2H, q), 6.46 (1H, q broad), 7.27 (2H, d), 7.50 (2H, d), 12.86 (1H, s broad).
6,7-dihydro-4-hydroxy-N-(3-pyridyl)-N,3,7-trimethyl-6-oxo-thieno[2,3-b]pyridine-5-carboxamide triethylamine salt, yield 94%; (reference substance, not according to the invention).
¹H NMR (D₂O): δ 0.86 (9H, t), 2.24 (3H, d broad) 2.37 (6H, q), 3.10 (3H, s), 3.29 (3H, s), 6.18 (1H, q broad), 7.10 (1H, dd), 7.67 (1H, dt), 8.00 (1H, dd), 8.34 (1H, d).
6,7-dihydro-4-hydroxy-N-phenyl-N,2,7-trimethyl-6-oxo-thieno[2,3-b]pyridine-5-carboxamide, yield 80%; not included in the claims.
¹H NMR (CDCl₃): δ 2.45 (3H, d), 3.22 (3H, s broad), 3.47 (3H, s), 6.95 (1H, q broad), 7.17-7.28 (5H, m), 12.10 (1H, s broad).
4,5-dihydro-N,4-dimethyl-7-hydroxy-N-phenyl-5-oxo-2-thia-4-aza-indene-6-carboxamide, yield 33%.
¹H NMR (CDCl₃): δ 3.15 (3H, s broad), 3.49 (3H, s), 6.49 (1H, d), 7.15-7.21 (3H, m), 7.24-7.30 (2H, m), 7.98 (1H, d), 12.36 (1H, s broad).
4,5-dihydro-N-ethyl-7-hydroxy-4-methyl-N-phenyl-5-oxo-2-thia-4-aza-indene-6-carboxamide, yield 30%.
¹H NMR (CDCl₃+TFA): δ 1.22 (3H, t), 3.45 (3H, s), 3.97 (2H, q), 6.85 (1H, d), 7.21-7.25 (3H, m), 7.28-7.32 (2H, m), 8.10 (1H, d).
N-(2,5-difluorophenyl)-4,5-dihydro-N,4-dimethyl-7-hydroxy-5-oxo-2-thia-4-aza-indene-6-carboxamide, yield 46%.
¹H NMR (CDCl₃): δ 3.22 (3H, s broad), 3.41 (3H, s), 6.55 (1H, d), 6.82-6.96 (2H, m), 7.02-7.11 (1H, m), 8.03 (1H, d), 12.41 (1H s broad).
N-(2,4-difluorophenyl)-4,5-dihydro-N,4-dimethyl-7-hydroxy-5-oxo-thieno[3,2-b]pyridine-6-carboxamide; yield 57%; (reference compound, not according to the invention).
¹H NMR (CDCl₃): δ 3.32 (3H, s broad), 3.38 (3H, s), 6.69 (1H, s broad), 6.87 (1H,t broad), 6.94 (1H, s broad), 7.04 (1H, s broad), 7.70 (1H, d), 12.46 (1H, s broad).

EXAMPLE 7

4,5-Dihydro-N,4-dimethyl-7-hydroxy-N-phenyl-5-oxo-thieno[3,2-b]pyridine-6-carboxamide (reference compound, not according to the invention) (Method B)

4,5-Dihydro-7-hydroxy-4-methyl-5-oxo-thieno[3,2-b]pyridine-6-carboxylic acid (1.27 mmol, 288 mg), N-methylaniline (1.92 mmol, 0.211 ml,) and dicyclohexylcarbodiimide (1.92 mmol, 0.41 g) were heated in toluene (3 ml) at 70° C. for 4 hrs. The mixture was cooled, 0.5 M sulphuric acid (20 ml) was added and then the mixture was extracted with chloroform. The organic phase was extracted with 1 M NaOH, pH was adjusted to about 6 and the precipitate of dicyclohexylurea was filtered off. The precipitate formed upon acidification with aqueous HCl was then collected and dried in vacuum to furnish the title compound (225 mg, 56%).

$^1$H NMR (CDCl$_3$): δ3.30 (3H, s broad), 3.47 (3H, s), 6.92 (1H, d), 7.13-7.21 (3H, m).

EXAMPLE 8

6,7-dihydro-4-hydroxy-N-phenyl-N,3,7-trimethyl-6-oxo-thieno[2,3-b]pyridine-5-carboxamide calcium salt 6,7-Dihydro-4-hydroxy-N-phenyl-N,3,7-triethyl-6-oxo-thieno[2,3-b]pyridine-5-carboxamide (0.304 mmol, 100 mg) was dissolved in a mixture of 1M NaOH (0.304 mmol, 0.304 ml) and ethanol (1 ml). The mixture was heated to 50° C. and aqueous 1M calcium acetate monohydrate (1.05 equiv., 0.16 mmol, 0.16 ml) was added dropwise with stirring. After stirring at 50° C. for 30 min the precipitate was filtered, washed with ethanol/water, and dried under vacuum to give the title compound (101 mg, 96%).

Anal. Calcd. For C$_{34}$H$_{30}$CaN$_4$O$_6$S$_2$; C, 58.77%; H, 4.35%; N; 8.06%. found C, 58.8; H, 4.73; N, 7.86. EDTA-titriometric determination of Ca gave 5.64% (theoretical 5.77%).

EXAMPLE 9

6,7-dihydro-4-hydrox-N-phenyl-N,3,7-trimethyl-6-oxo-thieno[2,3-b]pyridine-5-carboxamide diethanolamine salt 6,7-dihydro-4-hydroxy-N-phenyl-N,3,7-trimethyl-6-oxo-thieno[2,3-b]pyridine-5-carboxamide (0.304 mmol, 100 mg), methanol (3 ml) and diethanolamine (0.33 mmol, 0.032 ml) were mixed and the volatiles were removed. The residue was crystallised from ethyl acetate (2 ml) and heptane (5 ml) to give the title compound (101 mg, 76%). $^1$H-NMR in D$_2$O reveals two isomeric forms in a ratio of 4/1. Only signals from the major form are reported.

$^1$H-NMR (D$_2$O) (major rotamer) δ 2.37 (3H, s), 3.21 (4H, t), 3.26 (3H, s), 3.37 (3H, s), 3.85 (4H, t), 6.38 (1H, s), 7.10 (1H, t), 7.19 (2H, t), 7.33 (2H, d).

Anal. Calcd. For C$_{21}$H$_{27}$N$_3$O$_5$S; C, 58.18%; H, 6.28%; N, 9.69%. found C, 57.58; H, 6.40; N, 9.51.

EXAMPLE 10

6,7-dihydro-4-hydroxy-N-phenyl-N3,7-trimethyl-6-oxo-thieno[2,3-b]pyridine-5-carboxamide lithium salt 6,7-dihydro-4-hydroxy-N-phenyl-N,3,7-trimethyl-6-oxo-thieno[2,3-b]pyridine-5-carboxamide (0.304 mmol, 100 mg) and ethanol (0.48 ml) were stirred and a solution of lithium hydroxide hydrate (1.04 equiv., 13.2 mg) in water (0.26 ml) was added dropwise. After stirring for 5 min the mixture was concentrated and ethyl acetate (5 ml) was added. The precipitate was collected and dried to furnish the title compound (79 mg, 77%). $^1$H-NMR in D$_2$O reveals two isomeric forms in a ratio of 4/1. Only signals from the major form are reported.

$^1$H-NMR (D$_2$O) (major rotamer) δ 2.37 (3H, s), 3.25 (3H, s), 3.37 (3H, s), 6.37 (1H, s), 7.09 (1H, t), 7.19 (2H, t), 7.33 (2H, d).

EXAMPLE 11

6,7-dihydro-4-hydroxy-N-phenyl-N,3,7-trimethyl-6-oxo-thieno[2,3-b]pyridine-5-carboxamide sodium salt 6,7-dihydro-4-hydroxy-N-phenyl-N,3,7-trimethyl-6-oxo-thieno[2,3-b]pyridine-5-carboxamide (0.304 mmol, 100 mg) and 2-propanol (0.40 ml) were stirred and a solution of sodium methoxide in methanol (0.5 M, 0.305 mmol, 0.609 ml) was added. The mixture was concentrated, diethyl ether (2 ml) was added, and the mixture was sonicated for 15 min on an ultrasound bath. The resulting crystalline precipitate was collected by filtration and dried to give the title compound (49 mg, 46%). $^1$H-NMR in D$_2$O reveals two isomeric forms in a ratio of 4/1. Only signals from the major form are reported.

$^1$H-NMR (D$_2$O) (major rotamer) δ 2.37 (3H, s), 3.25 (3H, s), 3.37 (3H, s), 6.37 (1H, s), 7.09 (1H, t), 7.19 (2H, t), 7.33 (2H, d).

EXAMPLE 12

6,7-dihydro-4-hydroxy-N-phenyl-N,3,7-trimethyl-6-oxo-thieno[2,3-b]pyridine-5-carboxamide copper(II) salt 6,7-dihydro-4-hydroxy-N-phenyl-N,3,7-trimethyl-6-oxo-thieno[2,3-b]pyridine-5-carboxamide (0.304 mmol, 100 mg), water (1.0 ml), and 1M NaOH (0.304 mmol, 0.304 ml) were stirred and to the resulting clear solution was added a solution of copper(II)sulphate pentahydrate (0.152 mmol, 38.0 mg) in water (0.2 ml). A thick pale-green precipitate results. Chloroform (2.0 ml) was added which results in a clear colourless aqueous phase and a clear and greenish coloured organic phase. The organic phase was collected, dried, and evaporated. Upon treatment of the residue with methanol (2.0 ml) a green crystalline precipitate results which is isolated by filtration and dried to give the title product. NMR in CDCl$_3$ gave very broad signals probably due to the paramagnetic feature of copper(II).

EXAMPLE 13

6,7-dihydro-4-hydroxy-N-phenyl-N,3,7-trimethyl-6-oxo-thieno[2,3-b]pyridine-5-carboxamide iron(III) salt 6,7-dihydro-4-hydroxy-N-phenyl-N,3,7-trimethyl-6-oxo-thieno[2,3-b]pyridine-5-carboxamide (0.304 mmol, 100 mg), water (1.0 ml), and 1M NaOH (0.304 mmol, 0.304 ml) was stirred and to the resulting clear solution was added a solution of iron(III)sulphate pentahydrate (0.051 mmol, 0.102 mmol Fe(III), 25.0 mg) in water (0.1 ml). A thick red precipitate results. Chloroform (2.0 ml) was added which results in a clear colourless aqueous phase and a dark-reddish coloured organic phase. The organic phase was collected, dried, and evaporated. Upon treatment of the residue with diethylether (2.0 ml) a red crystalline precipitate results which is isolated by filtration and dried to give the title product (25.3 mg, 25%).

EXAMPLE 14

Acetic acid 6,7-dihydro-3,7-dimethyl-5-(methyl-phenyl-carbamoyl)-6-oxo-thieno[2,3-b]pyridin-4-yl ester.

6,7-Dihydro-4-hydroxy-N-phenyl-N,3,7-trimethyl-6-oxo-thieno[2,3-b]pyridine-5-carboxamide (0.76 mmol, 250 mg) was dissolved in pyridine (3 ml) and acetic anhydride (1 ml) was added. The reaction mixture was stirred at ambient temperature for 2 hrs after which 1 M HCl (aq) (20 ml) was added. The precipitate was collected by filtration, washed with water and dried to yield the title compound (209 mg, 74%).

$^1$H-NMR (CDCl$_3$) (major rotamer) δ 2.27 (3H, d), 2.38 (3H, s), 3.45 (3H, s), 3.46 (3H, s), 6.51 (1H, d), 7.14-7.42 (5H, m); (minor rotamer) δ 2.37 (3H, s), 2.38 (3H, s), 3.34 (3H, s), 3.71 (3H, s), 6.63 (1H, d), 7.14-7.42 (5H, m).

EXAMPLE 15

2,2-Dimethyl-propionic acid 6,7-dihydro-3,7-dimethyl-5-(methyl-phenyl-carbamoyl)-6-oxo-thieno[2,3-b]pyridine-4-yl ester.

6,7-Dihydro-4-hydroxy-N-phenyl-N,3,7-trimethyl-6-oxo-thieno[2,3-b]pyridine-5-carboxamide (0.76 mmol, 250 mg) was dissolved in pyridine (3 ml) and pivaloyl chloride (0.12 ml) was added. The reaction mixture was stirred at ambient temperature for 2 hrs after which 1 M HCl (aq) (20 ml) was added. The precipitate was collected by filtration, washed with water and dried to yield the title compound (116 mg, 37%).

$^1$H-NMR (CDCl$_3$) (major rotamer) δ 1.44 (9H, s),;2.25 (3H, d), 3.42 (3H, s), 3.46 (3H, s), 6.49 (1H, d), 7.17-7.41 (5H, m); (minor rotamer) δ 1.36 (9H, s), 2.37 (3H, d), 3.33 (3H, s), 3.72 (3H, s), 6.62 (1H, d), 7.17-7.41 (5H, m).

EXAMPLE 16

2,2-Dimethyl-propionic acid 6,7-dihydro-3,7-dimethyl-5-(methyl-phenyl-carbamoyl)-6-oxo-thieno[2,3-b]pyridin-4-yloxymethyl ester 6,7-Dihydro-4-hydroxy-N-phenyl-N,3,7-trimethyl-6-oxo-thieno[2,3-b]pyridine-5-carboxamide (0.76 mmol, 250 mg) was dissolved in DMF (3 ml). Chloromethyl pivaloate (1.14 mmol, 0.171 ml), 1,8-diazabicyclo[5.4.0]undec-7-ene (DBU, 1.14 mmol, 0.175 ml) and potassium iodide (10 mg) were added. The reaction mixture was stirred at ambient temperature for 72 hrs after which 1 M HCl (aq) (20 ml) was added. The precipitate was collected by filtration, washed with water and dried to yield the title compound (172 mg, 51%).

$^1$H-NMR (CDCl$_3$) (major rotamer) δ 1.25 (9H, s), 2.29 (3H, d), 3.50 (3H, s), 3.51 (3H, s), 5.85 (1H, d), 6.11 (1H, d), 6.43 (1H, d), 7.15-7.48 (5H, m); (minor rotamer) δ 1.25 (9H, s), 2.43 (3H, d), 3.47 (3H, s), 3.68 (3H, s), 5.86 (1H, d), 6.13 (1H, d), 6.56 (1H, d), 7.15-7.48 (5H, m).

Pharmaceutical Formulations

EXAMPLE 17

A pharmaceutical formulation according to the present invention, in the form of capsules, is prepared as follows: Compound #1 sodium is dissolved in excess aqueous sodium carbonate and wet granulated together with mannitol and additional sodium carbonate. All excipients required for capsule filling except the lubricant are present in the granulation step. The resulting granulate is dried in a conventional manner and passed through a screen of suitable size. The dry granules are mixed well with sodium stearyl fumarate and the mixture obtained is filled into capsules. The capsules contain suitable amounts of the active ingredient.

EXAMPLE 18

A pharmaceutical formulation according to the present invention, in the form of capsules, is prepared as follows: A preblend of Compound #1 calcium, mannitol and microcrystalline cellulose is prepared. The preblend is wet granulated with an aqueous calcium acetate solution. All excipients required for capsule filling are present in the granulation step. The resulting granulate is dried in a conventional manner and passed through a screen of suitable size. The dry granules are filled into capsules. The capsules contain suitable amounts of the active ingredient.

Pharmacological Methods

Acute Experimental Autoimmune Encephalomyelitis (aEAE).

SJL/N female mice, 8 weeks of age, were used for the experiments. Mouse spinal cord homogenate (MSCH) was obtained from 8 to 12 weeks-old C57B1/6 female mice. The tissue was homogenised on ice and diluted in cold PBS. Incomplete Freund's containing 1 mg/ml M. tuberculosis hominis H37Ra was emulsified with an equal volume of MSCH to give a final concentration of 10 mg/ml of MSCH. The inoculum volume of 0.1 ml was injected intradermally at the base of the tail. Pertussis toxin was injected i.p. at day 0 and 3 after immunisation. Treatment was given per os daily at days 3 to 7 and 10 to 12. Control animals received saline. The animals, eight per dose group, were scored for clinical signs of paralytic disease on a scale from 0 to 5 in the following way: 0, normal; 1, limp tail; 2, hind limb paresis; 3 bind limb paralysis and limp foreleg; 4, bilateral hind and fore limb paralysis; 5, death. Clinical scores were monitored at day 7 and daily from day 9 until the end of the experiment at day 14. Treatment effects were calculated as percent inhibition of clinical scores compared to saline treated controls.

Collagen Induced Arthritis.

DBA/1 male mice between 8 to 10 weeks of age were used for the experiments. On day 0 the mice were immunised intradermally at the base of the tail with bovine type II collagen (100 µg/mouse) in Freund's complete adjuvant. The treatment was given per os daily on days 3 to 7, 10 to 14, 17 to 21, 24 to 28 and 31 to 35. Fifteen days after immunisation mice were inspected for signs of arthritis. The animals were inspected three times a week. Every second or third day individual paws of the arthritic animals were scored by a scale from 0-4 (0=no arthritis, 1=arthritis in one of the interphalangeal, metatarsophalangeal or intercarpal joints, 2=two arthritic joints, 3=three arthritic joints, 4=as in 3 but with more severe redness and swelling of the paw). The score for each paw was added to give a maximal attainable score of 16 for each mouse.

R-3327 AT-1 Rat Prostatic Cancer

The Dunning R-3327 AT-1 is a prostatic cancer of the rat and suits as an experimental animal model for this disease in man. The AT-1 tumour is serially transplanted subcutaneously (sc) on syngeneic rats of the Copenhagen strain. Small pieces of the tumour are transplanted sc to recipient rats and treatment of the tumour bearing rats start when the tumours are easily measurable approximately on day 10 after transplantation. Doses of the compounds are given either orally or parentally 5 days a week for four weeks. The tumour growth and body weight gain are monitored during the experimental time.

The thieno[2,3-b]pyridine and 2-thia-4-aza-indene derivatives were tested for their ability to inhibit aEAE in mice following treatment at different doses. Table 2 summarises aEAE screening data Among preferred compounds are 6,7-dihydro-4-hydroxy-N-phenyl-N,3,7-trimethyl-6-oxo-thieno[2,3-b]pyridine-5-carboxamide (compound #1), 6,7-dihydro-3,7-dimethyl-N-ethyl-4-hydroxy-N-phenyl-6-oxo-thieno[2,3-b]pyridine-5-carboxamide (compound #2), 6,7-dihydro-N,7-dimethyl-3-ethyl-4-hydroxy-N-phenyl-6-oxo-thieno[2,3-b]pyridine-5-carboxamide (compound #3), 6,7-dihydro-4-hydroxy-N-(4-methoxyphenyl)-N,3,7-trimethyl-6-oxo-thieno[2,3-b]pyridine-5-carboxamide (compound #6) and 4,5-dihydro-7-hydroxy-N-phenyl-N,1,4-trimethyl-5-oxo-2-thia-4-aza-indene-6-carboxamide (compound #10). Furthermore, to illustrate the inventive step, the inventive compound 6,7-dihydro-N,7-dimethyl-4-hydroxy-N-phenyl-6-oxo-thieno[2,3-b]pyridine-5-carboxamide (compound #11) and the reference compounds (not according to the invention) 4,5-dihydro-N,4-dimethyl-7-hydroxy-N-phenyl-5-oxo-thieno[3,2-b]pyridine-6-carboxamide (compound #12) and 6,7-dihydro-4-hydroxy-N-(3-pyridyl)-N,3,7-trimethyl-6-oxo-thieno[2,3-b]pyridine-5-carboxamide (compound #13) are included.

TABLE 2 aEAE inhibition.

| Compound | aEAE inhibition (%) Dose (mg/kg po) | | |
|---|---|---|---|
|  | 0.2 | 1.0 | 5.0 |
| #1 (invention) | 85 | 99 |  |
| #2 (invention) | 66 | 84 |  |
| #3 (invention) | 84 | 100 |  |
| #6 (invention) | 92 |  |  |
| #10 (invention) |  | 78 | 95 |
| #11 (reference) |  | 53 |  |
| #12 (reference) |  |  | inactive* |
| #13 (reference) |  |  | 46 |

*inactive is defined as <35% inhibition.

Effective quantities of the compounds of formula (I) are preferably administered to a patient in need of such treatment according to usual routes of administration and formulated in usual pharmaceutical compositions comprising an effective amount of the active ingredient and suitable pharmaceutically acceptable nontoxic excipients and carriers. Such compositions may take a variety of forms, e.g. solutions, suspensions, emulsions, tablets, capsules, and powders prepared for oral administration, aerosols for inhalations, sterile solutions for parental administration, suppositories for rectal administration or suitable topical formulations. The concentration of the compounds described herein in a therapeutic composition will vary depending upon a number of factors, including the dosage of the drug to be administered, the chemical characteristics of the compound employed, and the route of administration. Conventional procedures for the selection and preparation of suitable pharmaceutical formulations are described, for example, in "Pharmaceuticals—The Science of Dosage Form Design", M. B. Aulton, Churchill Livingstone, 1988.

The composition, may conveniently be administered in unit dosage form. The preferred dosage of the drug to be administered is likely to depend on such variables as the type and extent of progression of the disease or disorder, the overall health status of the particular patient, the relative biological efficacy of the compound selected, and formulation of the compound excipient, and its route of administration. A suitable daily dose for use in the treatment of the above mentioned diseases is contemplated to vary between 0.0005 mg/kg to about 10 mg/kg body weight, in particular between 0.005 mg/kg to 1 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

Some thieno[2,3-b]pyridine-5-carboxamide and 2-thia-4-aza-indene-6-carboxamide derivatives are susceptible to chemical degradation in a solid pharmaceutical formulation. In one embodiment of the present invention, as illustrated in Examples 17 and 18 herein above, this problem is solved by the provision of a process for preparing a stable solid pharmaceutical formulation that contains a salt of a thieno[2,3-b]pyridine-5-carboxamide or 2-thia-4-aza-indene-6-carboxamide derivative of formula (I) with a monovalent or multivalent cation. The process comprises forming a capsule or a tablet containing a salt of a thieno[2,3-b]pyridine-5-carboxamide or 2-thia-4-aza-indene-6-carboxamide derivatives and a uniformly distributed alkaline-reacting component, such as sodium carbonate, capable of neutralising any protons dissociating from the excipients, thereby keeping the thieno[2,3-b]pyridine-5-carboxamide or 2-thia-4-aza-indene-6-carboxamide derivatives in the salt form.

REFERENCES

1. Talal, N.: Autoimmune diseases. In: Roitt, I. M. and Delves, P. J. (eds.) Encyclopedia of Immunology, pp. 195-198. Academic Press, 1992.
2. Prineas, J. W.: The neuropathology of multiple sclerosis. In: Koetsier, J. C. (ed.) Handbook of Clinical Neurology, pp. 213-257. Elsevier Science Publ., Amsterdam, 1985.
3. Gutschow, M. et al., J. Med. Chem. 1999, 42, 5437-5447.
4. Gewald, K. et al., Chem. Ber. 1966, 99, 94-100.
5. Shinkwin, A. E. et al., Bioorg. Med. Chem. 1999, 7, 297-308.
6. Buchstaller, H.-P. et al., Monatsh. Chemic 2001, 132, 279-293.
7. Liu, H.-J. et al., Can. J. Chem., 1982, 60, 437-439.
8. Johnstone, R. A. W. et al., J. Chem. Soc. 1969, 2223-2224.

The invention claimed is:
1. A compound of formula (I)

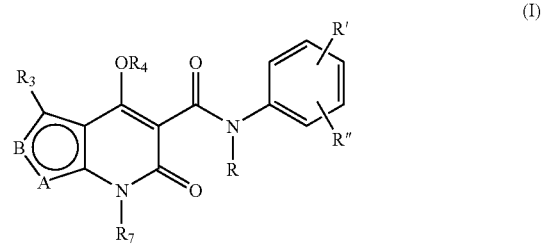

wherein
R is selected from methyl, ethyl, n-propyl, iso-propyl, n-butyl and allyl;

R' is selected from hydrogen, straight, branched or cyclic $C_1$-$C_4$ alkyl; straight, branched or cyclic $C_1$-$C_3$ alkoxy; fluoro, chloro, bromo, trifluoromethyl and $OCH_xF_y$,
wherein x=0, 1, 2,
y=1, 2, 3 with the proviso that
x+y=3;
R" is selected from hydrogen, fluoro and chloro, with the proviso that R" is selected from fluoro and chloro only when R' is selected from floro and chloro;
$R_3$ is selected from hydrogen and straight, branched or cyclic $C_1$-$C_5$ alkyl;
$R_4$ is hydrogen, $CH_2OCOC(CH_3)_3$, or $COR_4'$ wherein $R_4'$ is straight or branched $C_1$-$C_5$ alkyl, phenyl, benyl or phenethyl;
$R_7$ is methyl or ethyl;
B is C—$R_2$;
A is S, $R_2$ is hydrogen or methyl, with the proviso that $R_2$ is methyl only
when $R_3$ is not hydrogen;
and any tautomer thereof.

2. A compound according to claim 1 wherein R' is hydrogen, straight, branched or cyclic $C_1$-$C_3$ alkyl; straight, branched or cyclic $C_1$-$C_3$ alkoxy; fluoro, chloro, bromo, trifluoromethyl or $OCH_xF_y$.

3. A compound according to claim 1 or claim 2 wherein R' is para-methoxy, para-fluoro, para-chloro, para-trifluoromethyl or para-trifluoromethoxy when R" is hydrogen.

4. A compound according to claim 1 wherein R" is ortho-fluoro and R' is para- or meta'-fluoro.

5. A compound according to claim 1 wherein $R_3$ is straight, branched or cyclic $C_1$-$C_4$ alkyl.

6. A compound according to claim 5 wherein $R_3$ is methyl, ethyl, iso-propyl or tert-butyl.

7. A compound according to claim 1 wherein R is methyl or ethyl.

8. A compound according to claim 1 wherein $R_7$ is methyl.

9. The compound according to claim 1, which is 6,7-dihydro-4-hydroxy-N-phenyl-N,3,7-trimethyl-6-oxo-thieno[2,3-b]pyridine-5-carboxamide.

10. The compound according to claim 1 which is 6,7-dihydro-3,7-dimethyl-N-ethyl-4-hydroxy-N-phenyl-6-oxo-thieno[2,3-b]pyridine-5-carboxamide.

11. The compound according to claim 1, which is 6,7-dihydro-N,7-dimethyl-3-ethyl-4-hydroxy-N-phenyl-6-oxo-thieno[2,3-b]pyridine-5-carboxamide.

12. The compound according to claim 1, which is N,3-diethyl-6,7-dihydro-4-hydroxy-7-methyl-N-phenyl-6-oxo-thieno[2,3-b]pyridine-5-carboxamide.

13. The compound according to claim 1, which is 6,7-dihydro-N,7-dimethyl-4-hydroxy-3-iso-propyl-N-phenyl-6-oxo-thieno[2, 3-b]pyridine-5-carboxamide.

14. The compound according to claim 1, which is 6,7-dihydro-4-hydroxy-N-(4-methoxyphenyl)-N,3,7-trimethyl-6-oxo-thieno[2,3-b]pyridine-5-carboxamide.

15. The compound according to claim 1, which is N-(2,4-difluorophenyl)-6,7-dihyro-4-hydroxy-N,3,7-trimethyl-6-oxo-thieno[2,3-b]pyridine-5-carboxamide.

16. The compound according to claim 1, which is 6,7-dihydro-4-hydroxy-N-(4-methyiphenyl)-N,3,7-trimethyl-6-oxo-thieno[2,3-b]pyridine-5-carboxamide.

17. The compound according to claim 1, which is 6,7-dihydro-4-hydroxy-N-(4-trifluoromethoxyphenyl)-N,3,7-trimethyl-6-oxo-thieno[2,3-b]pyridine-5-carboxamide.

18. The compound according to claim 1, which is N-(4-chlorophenyl)-6,7-dihydro-4-hydroxy-N,3,7-trimethyl-6-oxo-thieno[2,3-b]pyridine-5-carboxamide.

19. A compound of formula (I)

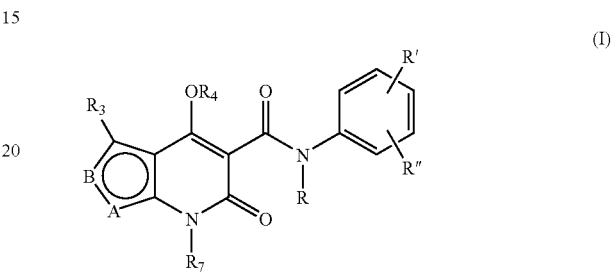

wherein
R is methyl, ethyl, n-propyl, iso-propyl, n-butyl or allyl;
R' is hydrogen, straight, branched or cyclic $C_1$-$C_4$ alkyl; straight, branched or cyclic $C_1$-$C_3$ alkoxy; fluoro, chloro, bromo, trifluoromethyl or $OCH_xF_y$,
wherein x=0, 1, 2,
y=1, 2, 3 with the proviso that
x+y=3;
R" is hydrogen, fluoro or chloro, with the proviso that R" is fluoro or chloro only when R' is floro or chloro;
$R_3$ is hydrogen or straight, branched or cyclic $C_1$-$C_5$ alkyl;
$R_4$ is hydrogen, $CH_2OCOC(CH_3)_3$, lithium, sodium, potassium, magnesium, calcium, copper (II), zinc, aluminum, iron (III), monoethanolamine, diethanolamine, or $COR_4'$ wherein $R_4'$ is straight or branched $C_1$-$C_5$ alkyl, phenyl, benyl or phenethyl;
$R_7$ is methyl or ethyl;
A is sulphur and B is C—$R_2$;
$R_2$ is hydrogen or methyl, with the proviso that $R_2$ is methyl only
when $R_3$ is not hydrogen;
and any tautomer thereof.

20. A compound according to claim 19 wherein $R_4$ is sodium or calcium.

21. Pharmaceutical composition comprising as active ingredient a compound according to any one of claims 1, 2, 4-20 or 9-18, together with pharmaceutically acceptable non-toxic excipients and carriers.

* * * * *

UNITED STATES PATENT AND TRADEMARK OFFICE
CERTIFICATE OF CORRECTION

PATENT NO. : 7,553,849 B2  
APPLICATION NO. : 11/152777  
DATED : June 30, 2009  
INVENTOR(S) : Bjork et al.

Page 1 of 1

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 554 days.

Delete the phrase "by 554 days" and insert -- by 934 days --

Signed and Sealed this

First Day of June, 2010

David J. Kappos  
*Director of the United States Patent and Trademark Office*